(12) United States Patent
Brizard et al.

(10) Patent No.: US 9,220,809 B2
(45) Date of Patent: Dec. 29, 2015

(54) USE OF A FLUORINATED POLYMER AS A CONTRAST AGENT IN SOLID STATE 19F MAGNETIC RESONANCE IMAGING (MRI), SCAFFOLD COMPRISING SAID POLYMER AND USE THEREOF

(75) Inventors: Aurelie Brizard, Eindhoven (NL); Emial Pesters, Eindhoven (NL); Dirk Jan Broer, Eindhoven (NL); Rudolf Mathias Johannes Nicolaas Lamariche, Eindhoven (NL); Anton William Bosman, Eindhoven (NL); Henricus Marie Janssen, Eindhoven (NL); Serge Hendrikus Mathÿs Söntjens, Eindhoven (NL)

(73) Assignees: XELTIS BV (NL); SUPRAPOLIX B.V. (NL); KONINKLIJKE PHILIPS N.V. (NL)

(*) Notice: Subject to any disclaimer, the term of this patent is extended or adjusted under 35 U.S.C. 154(b) by 1 day.

(21) Appl. No.: 13/310,282

(22) Filed: Dec. 2, 2011

(65) Prior Publication Data

US 2012/0148500 A1     Jun. 14, 2012

Related U.S. Application Data

(60) Provisional application No. 61/419,444, filed on Dec. 3, 2010.

(30) Foreign Application Priority Data

Dec. 3, 2010    (EP) ..................................... 10193654

(51) Int. Cl.
| | |
|---|---|
| A61K 49/12 | (2006.01) |
| C08L 27/12 | (2006.01) |
| A61L 27/26 | (2006.01) |
| A61L 27/50 | (2006.01) |

(52) U.S. Cl.
CPC ............... *A61L 27/26* (2013.01); *A61K 49/126* (2013.01); *A61L 27/50* (2013.01)

(58) Field of Classification Search
CPC ......... A61K 49/12; A61K 51/06; C08L 27/12
USPC ........... 424/1.89, 9.1, 9.3, 423; 600/420, 431, 600/433, 435; 623/1.15, 1.42, 23.7
See application file for complete search history.

(56) References Cited

U.S. PATENT DOCUMENTS

| | | | |
|---|---|---|---|
| 6,574,497 | B1 | 6/2003 | Pacetti |
| 2011/0153027 | A1* | 6/2011 | Behan ......................... 623/23.7 |
| 2011/0182805 | A1* | 7/2011 | Desimone et al. ........... 424/1.11 |
| 2011/0243852 | A1* | 10/2011 | Peeters et al. .................. 424/9.1 |
| 2012/0136120 | A1* | 5/2012 | Bosman ....................... 525/123 |

FOREIGN PATENT DOCUMENTS

| | | |
|---|---|---|
| WO | WO-00/59963 | * 10/2000 |
| WO | WO2006/002332 A1 | 1/2006 |
| WO | WO2006/118461 A2 | 11/2006 |
| WO | WO2006/119645 A1 | 11/2006 |
| WO | WO2008/016983 A2 | 2/2008 |
| WO | WO2010/058361 A2 | 5/2010 |
| WO | WO2010/070522 A1 | 6/2010 |

OTHER PUBLICATIONS

Joseph M. DeSimones et al. Solvent-Resistant Photocurable "Liquid Teflon" for Microfluidic Device Fabrication, J. Am.Chem.Soc., 2004, 126, 2322-2323.*

Hugo Fernandes et al., Extracellular matrix and tissue engineering applications, (J. Mater. Chem, 19, 5474-5484, 2009).*

European Search Report dated May 12, 2011 issued by the European Patent Office for parent application No. EP10193654.0.

* cited by examiner

*Primary Examiner* — Michael G Hartley
*Assistant Examiner* — Jagadishwar Samala
(74) *Attorney, Agent, or Firm* — Wilson Sonsini Goodrich & Rosati (57) ABSTRACT

A method of using a fluorinated polymer having a glass transition temperature below 40 C as a contrast agent in $^{19}$F magnetic resonance imaging (MRI) of a solid object, said solid object comprising said contrast agent. The invention relates to a solid object comprising a structural component and an imaging component, wherein the imaging component is at least one fluorinated polymer. The invention relates to a method for $^{19}$F MRI in solid state using a contrast agent comprising a fluorinated polymer as well as a method for in vivo visualizing a scaffold. It further relates to a method for in vivo monitoring the degradation of a solid object in time, wherein the degradation is monitored in time by using $^{19}$F MRI to visualize the solid object, and wherein the amount of degradation of the solid object is determined based on the decrease in the visibility of the amount of $^{19}$F.

10 Claims, 6 Drawing Sheets

USE OF A FLUORINATED POLYMER AS A CONTRAST AGENT IN SOLID STATE 19F MAGNETIC RESONANCE IMAGING (MRI), SCAFFOLD COMPRISING SAID POLYMER AND USE THEREOF

CROSS-REFERENCE TO RELATED APPLICATION

This non-provisional patent application claims priority from provisional patent application No. 61/419,444 filed on Dec. 3, 2010, and European patent application no. 10193654.0 filed Dec. 3, 2010, which are relied upon and incorporated herein by reference.

REFERENCE TO JOINT RESEARCH AGREEMENT

The inventions described herein were made pursuant to a joint research agreement among SUPRAPOLIX B.V.; QTIS/E B.V.; and KONINKLIJKE PHILIPS ELECTRONICS N.V.

FIELD OF THE INVENTION

The present invention relates to the use of a fluorinated polymer as a contrast agent for $^{19}$F magnetic resonant imaging (MRI) in a solid object. The present invention furthermore relates to a scaffold suitable for tissue engineering, said scaffold comprising a structural component and an imaging component, the imaging component being at least one fluorinated polymer.

In addition, the present invention relates to a method for $^{19}$F magnetic resonance imaging (MRI) in solid state using a contrast agent comprising a fluorinated polymer.

The present invention furthermore relates to a method for in vivo visualization of a solid object or scaffold as well as for a method for in vivo monitoring of the degradation of a solid object or scaffold in time.

The present invention may be applicable in the field of tissue engineering for monitoring post-implantation remodelling of tissue engineering substitutes or for monitoring in-vivo degradation of scaffold materials or implants such as stents or drug eluting devices (i.e. a device that releases one or more drugs over a period of time).

BACKGROUND OF THE INVENTION

Over recent years continuous improvements in our healthcare have resulted in dramatic demographic changes, e.g. an increase in the average age of the population. These demographic changes are causing an increase in the prevalence of diseases associated with aging. Many of these diseases arise from the loss or dysfunction of specific cell types in the human body, leading to permanently damaged tissues and organs.

A relatively new field of medicine—since the early 1990s—is the field of Regenerative Medicine. Regenerative Medicine is the process of creating living and functional tissues to repair, replace, or restore tissue or organ structure and function lost due to age, disease, damage, or congenital defects. This field of medicine uses new methods including (stem) cell therapy, development of medical devices and tissue engineering.

The technique of tissue engineering consists of constructing substitutes (e.g. biological substitutes) for diseased tissues. Tissue engineering makes use of natural or polymeric scaffolds that provide mechanical support and promote the re-growth of cells lost due to trauma or disease. A scaffold is a temporary structure used to support material (e.g. tissue) during the recovery thereof.

A tissue engineering scaffold is usually implanted in vivo at the site in question and is slowly populated with cells, either by capturing progenitor cells form circulation or by in-growth of cells from neighbouring, healthy, tissue. Alternatively, the scaffolds can be pre-seeded in vitro with the appropriate cells prior to implantation. In most cases, as the formation and the remodelling of the newly formed tissue proceeds, degradation of the scaffold should slowly and steadily take place, leaving only new healthy tissue behind. With degradation is meant the breakdown of the material into smaller parts, e.g. chemical compounds and/or elements that can be eliminated from the body by means of excretion in urine for example. The degradation can be effected by the conditions in the body, such as the presence of water combined with the use of water-degradable material for the scaffold.

In order to monitor how fast the in vivo degradation of the scaffolds proceeds and in order to judge the ultimate success of the tissue engineering procedure, it is essential to develop scaffolding materials that are visible in relevant clinical imaging techniques, such as computed tomography (CT), magnetic resonance imaging (MRI) and/or diagnostic sonography (or ultrasonography) using ultrasound for imaging purposes, for example.

Since both natural and polymeric scaffolds themselves deliver little or no contrast compared to the surrounding tissues—because they are closely related in structure and material—imaging labels are required as contrast agents within the scaffolds. An imaging label is an identifying marker that may be attached to a material to be identified.

It is an aim of the present invention to provide an imaging label or contrast agent that can be used in solid objects, for instance in scaffolds.

It is a further aim of the present invention to provide a solid object, for instance a scaffold including an imaging component or contrast agent that can be visualized in clinical imaging techniques.

One or more of the above aims have been reached by the present invention.

The inventors have surprisingly found that it is possible to use $^{19}$F MRI for solid objects using fluorinated polymers as contrast agents or imaging labels.

BRIEF DESCRIPTION OF THE DRAWINGS

The present invention is illustrated in more detail in the following description and with reference to the drawings, in which:

FIG. 4(a) top is a photograph of Polymer 1 in solid state and FIG. 4(a) bottom is a $^{19}$F MRI scan of Polymer 1 in solid state.

FIG. 11 (a) is an optical microscope photo of electrospun fibres of Mix 1; FIG. 11 (b) is a $^{19}$F MRI image of Mix 1.

DETAILED DESCRIPTION OF THE INVENTION

In the present description and appended claims, the following terms are used, which are explained below.

"Fluorinated" means a hydrocarbon moiety in which some hydrogen atoms have been replaced by fluorine on a carbon chain.

A "polymer" is intended to also include copolymer or supramolecular polymer unless otherwise stated.

A "supramolecular polymer" is a compound or a polymer, usually of lower molecular mass, that exhibits properties that are not commonly associated with such low molecular mass compounds or polymers, but that are commonly associated with polymers of higher molecular mass. This effect is due to the self-assembly of the lower molecular mass compounds or polymers, for example due to strong hydrogen bonding interactions. As a result of the self-assembly, a (much) higher virtual molecular mass of the material is achieved. Examples of supramolecular polymers have been described in, for example, Science, 1997, 278, 1601.

"Perfluorinated" means a hydrocarbon moiety in which essentially all hydrogen atoms have been replaced by fluorine on a carbon chain.

The "glass transition temperature", or Tg, is the temperature at which glass transition takes place, being the dynamic phenomenon occurring between two distinct states of matter (liquid and glass), each with different physical properties. It can also be described as the temperature at which the Gibbs free energy is such that the activation energy for the cooperative movement of 50 or so elements of the polymer is exceeded.

"Differential scanning calorimetry" (DSC) is a thermoanalytical technique in which the difference in the amount of heat required to increase the temperature of a sample and a reference sample is measured as a function of the temperature. DSC can be used to assess the Tg of a material, and it can also be used to assess the melting temperatures or melting transitions of materials.

A "contrast agent" is a substance used to enhance the contrast of structures or fluids within the body in medical imaging.

A "scaffold" is a temporary structure used to support material (e.g. tissue) during the formation and/or recovery of said material.

A "structural component" is the part of the scaffold that is intended for the provision of structural properties.

An "imaging component" is the part of the scaffold that is intended for the provision of imaging properties.

A "biologically active component" is the part of the scaffold that is intended for the provisional of biological activity.

A "substrate" is the material on which growing of cells takes place.

A "solid object" is an object that is in the solid state and not in the liquid or gaseous state. The object preferably has a volume of at least 0.01 mm$^3$, more preferably at least 1 mm$^3$ and most preferably at least 10 mm$^3$. The object according to the present invention may or may not have holes or spaces or may or may not be hollow. The object according to the present invention may or may not be of the same substance throughout, i.e. it may contain one or more materials.

The present invention allows the visualisation of e.g. scaffolding materials in the solid state by making use of fluorinated polymers, such as fluorinated copolymers or fluorinated supramolecular polymers, which fluorinated polymers also serve as a contrast agent in $^{19}$F MRI. The presence of the fluorinated units present within (e.g. embedded in) the polymer matrix enables the in vivo monitoring of the structural integrity as well as the degradation process of implanted tissue engineering scaffolds in relation to the growth and remodelling of the newly formed tissue, therefore solving the problem of a so far unmet clinical need.

Fluorine-19, abbreviated as $^{19}$F, is the most stable isotope of fluorine. No other isotopes of fluorine exist in significant quantities. Fluorine-19 is NMR- and MRI-active and is used in fluorine-19 NMR spectroscopy.

The present inventors have found that fluorinated compounds, oligomers or polymers are very suitable as contrast agents since they enhance the visibility of tissue engineering scaffolds in $^{19}$F MRI. Fluorinated contrast agents benefit from the lack of background signal in tissue—since there is no native fluorine present in tissues—and further benefit from a high gyromagnetic ratio which makes $^{19}$F MRI a very sensitive technique. The gyromagnetic ratio arises from the nuclear spin of the F-nucleus and is defined as the ratio of the nuclear magneton over the reduced Planck constant (h-bar or the Dirac constant being equal to the Planck constant divided by $2\pi$) which is multiplied by the g-factor of the nucleus.

The gyromagnetic ratio of a nucleus is particularly important because of the role it plays in Magnetic Resonance Imaging (MRI). This imaging technique relies on the fact that nuclear spins precess in a magnetic field at a rate called the Larmor frequency, being the product of the gyromagnetic ratio with the magnetic field strength.

Magnetic resonance imaging is a non-invasive medical imaging technique frequently used in radiology to visualize detailed internal structures of the body. MRI provides a higher contrast between the different soft tissues of the body than computed tomography (CT) does, making MRI especially useful in neurological, musculoskeletal, cardiovascular, and oncological imaging.

The present invention is in a preferred embodiment aimed at the use of $^{19}$F MRI on a human or animal body, that is implanted with a solid object according to the present invention. In order for fluorine-19 MRI to work sufficiently, it is important that there is adequate mobility of the fluorinated polymer within the solid object. The requirement of fluorine mobility is for example described by K. L. Wooley et al. (Journal of Polymer Science: Part A, 2009, 47, 1023).

The present inventors have found that it is possible to prepare fluorinated polymer containing materials in the solid state in which the fluorinated polymer parts of the material have a certain mobility. In order for this mobility to be adequate, it is essential that the glass transition temperature of the fluorinated polymer is below 40° C., preferably below body temperature, or even below 20° C., more preferably below 0° C., or even below −40° C. If the fluorine mobility is not adequate, anisotropy would be the result, leading to undesirable peak broadening and inadequate imaging.

Normal human body temperature, also known as normothermia or euthermia, is a concept that depends upon the place in the body at which the measurement is carried out, on the time of day, and on the level of activity of the person in question. There is no single number that represents a normal or healthy temperature for all people under all circumstances using any place of measurement. However, the commonly accepted average body temperature of a human being (when taken internally) is 37.0° C.

The present invention is also applicable for use in animals, preferably mammals, such as domestic animals or cattle, for example. The body temperature of these animals can vary and will be known by a person skilled in the art.

A preferable lower limit of the glass transition temperature is −160° C., preferably −125° C.

In a first embodiment of the invention, the present inventors propose the use of fluorinated polymers and/or fluorinated copolymers, that are preferably based on biocompatible polymers. In a second embodiment of the invention, the present inventors propose the use of fluorinated supramolecular polymers (self-assembled molecules). All of these types of fluorinated polymers according to the invention are suitable for tissue engineering scaffolds.

An advantage of the fluorinated polymers according to the first and second embodiments mentioned above (i.e. the copolymers and supramolecular polymers) is that the fluorine part—i.e. the part that acts essentially as the contrast agent—is intrinsically part of the polymer backbone, prior to implantation of a solid object prepared with this fluorinated polymer. This property makes it easier to follow the degradation of the solid object in time, since the loss of the $^{19}$F MRI signal is directly and quantitatively related to the loss of material. Additionally, the incorporation of fluorinated units directly in the backbone of the polymeric chain should limit the hydrophobicity of the material, and thus favour cell adhesion; which is desirable when the polymer is used in scaffolds suitable for use as substrates for cell growth.

It is a further advantage of the present invention that it provides a contrast agent that allows quantitative in vivo monitoring of the degradation of the scaffolds in time.

It is a further advantage of the present invention that it provides a contrast agent which can be used in an animal or human body, even for a prolonged period of time and upon degradation of the solid object.

In a preferred embodiment, the amount of fluorine ($^{19}$F) in the fluorinated polymer is at least 5 wt %, based on the total mass of the polymer. This means that the combined mass of all atoms in the fluorinated polymer (including the fluorine atoms) is taken as 100 wt % and the mass of all fluorine atoms (number of atoms times 19 gram/mol) is divided by the total mass of all atoms in the fluorinated polymer.

This minimal amount of fluorine ensures adequate visibility in $^{19}$F MRI. The present inventors have carried out experiments showing that when 3 or 4 wt % of fluorine is used, the contrast of the MRI picture may not be not adequate.

More preferably, the amount of fluorine in the fluorinated polymer is at least 7 wt %, even more preferably at least 9 wt %, or at least 11 wt %. The higher the amount of fluorine, the better the contrast and the signal-to-noise ratio of the MRI experiment.

If however, the amount of fluorine is too high in the fluorinated polymer (either alone or according to the first and second embodiments disclosed above) such as more than 50 wt % or for example more that 60 wt % or even more than 70 wt %, the fluorinated polymer could become less biocompatible.

The fluorinated polymer may be obtained from at least one monomer selected from the group consisting of (per)fluoroethers, (per)fluoroesters, (per)fluoro-(meth)acrylates, (per)fluoroalkyls, preferably (per)fluoroethers.

The fluorinated polymer may be a homopolymer or a copolymer of any of these monomers or a copolymer of one or more of these (per)fluorinated monomers in combination with other non-fluorinated monomers, such as at least one monomer selected from the group consisting of esters, ethers, alcohols, lactones, preferably caprolactones or lactides, carbonates, amides, ureas, urethanes and combinations thereof.

Hence the fluorinated polymer as mentioned in the present invention may be a (per)fluorinated polymer obtained from one or more (per)fluorinated monomers. In addition, the fluorinated polymer may be a fluorinated copolymer obtained from co-polymerisation of at least one (per)fluorinated monomer and at least one non-fluorinated monomer. The polymerisation may be any type of polymerisation and the fluorinated copolymer may be an alternating copolymer, a block copolymer or a random copolymer. Moreover, the fluorinated polymer may be a fluorinated supramolecular polymer obtained via interactions between at least one fluorinated oligomer or polymer and at least one non fluorinated oligomer or polymer. With oligomer is meant at least 4 repeating units.

The use of the (per)fluorinated monomers mentioned above is advantageous since they are biocompatible and therefore applicable for use in a human or animal body. In perfluorinated monomers essentially all hydrocarbon atoms on the carbon chain have been replaced by fluorine atoms. This ensures the presence of an adequate amount of fluorine within the fluorinated polymer as required for acceptable MR imaging.

In yet another embodiment, the solid object further comprises at least one non-fluorinated polymer. The solid object may for example be prepared from a blend of at least one fluorinated (co)polymer and at least one non-fluorinated polymer. This makes it possible to obtain adequate structural properties in addition to adequate imaging properties.

In yet another embodiment, the fluorinated polymer and/or the at least one non-fluorinated polymer or the fluorinated blocks and/or the non-fluorinated blocks of the fluorinated polymer are bonded together by covalent bonding, non-covalent bonding, optionally by hydrogen bonding interactions, or a combination thereof. In the embodiment where the fluorinated polymer and/or the non-fluorinated polymer possess hydrogen bonding units, these units are selected from the group consisting of urethane, amide, urea, particularly bisurea, or ureidopyrimidone units and combinations thereof.

In yet another embodiment, the fluorinated polymer and the at least one non-fluorinated polymer are blended or mixed together to form said solid object.

According to the above, the fluorinated polymers of this invention have structural components so that indeed solid objects can be prepared from these fluorinated polymers. The solid behaviour of the fluorinated polymers may be due to covalent or non-covalent bonds between the polymer chains (i.e. chemical or physical crosslinks, such as particularly hydrogen bonding physical interactions), and/or it may be due to the presence of non-fluorinated polymers or non-fluorinated blocks that have Tg-values exceeding 50° C., preferably exceeding 70° C., more preferably exceeding 90° C., and/or it may be due to the presence of non-fluorinated polymers or non-fluorinated blocks that have melting transitions exceeding 20° C., preferably exceeding 30° C., more preferably exceeding 50° C. Preferably, the solid behaviour stems from hydrogen bonding interactions between the polymer chains and/or from the presence of melting transitions In the non-fluorinated polymer or blocks.

A variety of fluorinated or perfluorinated compounds, oligomers or polymers, such as perfluoro-octyl-bromide (PFOB) and poly-tetra-fluoro-ethene (PTFE, also known as Teflon), for example, are known to be inert and are considered to be biocompatible materials. The present inventors have found that fluorinated polymers may be incorporated in solid objects, such as scaffolds, for implantation in a human or animal body for tissue engineering, as a contrast agent. This allows following the progressive (i.e. happening steadily) degradation of said scaffolds or implants, without risk of long term toxicity caused by the contrast agent. This present invention thus relates to the use of fluorinated polymers both as a scaffold material for tissue engineering and as a contrast agent for $^{19}$F MRI.

In the embodiment of the present invention that uses fluorinated copolymers, these copolymers consist on the one hand of a repetition of highly fluorinated (or perfluorinated) oligomeric or polymeric units (A), such as (per)fluoroalkyl, (per)fluoroalkylene, (per)fluoroester, (per)fluoroether, or (per)fluoro-polyether units. These copolymers consist on the other hand of a polymeric unit (B) based on preferably biocompatible polymers, such as polyesters, polyethers, polyalcohols or polyurethane. A perfluoroalkyl (A) unit can, for example, be —$(CF_2)_n$— in which n is at least 4, preferably 5, more preferably 6 or 8. A perfluorether unit (A) can consist of —$(OCF_2)_n$— and/or —$(OCF_2CF_2)_n$— groups in which n is at least 5, more preferably at least 10. The general structure of the resulting fluorinated polymer can, for example, be: -(A-B)$_n$— or -(A)$_n$(B)$_m$—, wherein both n and m are integers. Accordingly, the A and B units can be organized in an alternating, segmented, blocked or random fashion, or in a combination thereof, preferably in a random fashion. The connections between the A and B units may be freely chosen, and may involve ether, urethane, amide and/or ester bonds, for example. The fluorinated copolymer has preferably a Young's modulus that is at least 0.1 Mega Pascal (MPa), preferably at least 1 MPa, most preferably at least 5 MPa. In this embodiment, the fluorinated copolymer preferably has a molecular mass of at least 2000 gram/mol, more preferably at least 4000 gram/mol, even more preferably at least 10,000 gram/mol. The molecular mass of the copolymer is preferably lower than 100,000 gram/mol, more preferably lower than 60,000 gram/mol, even more preferably lower than 40,000 gram/mol.

Figure 1:
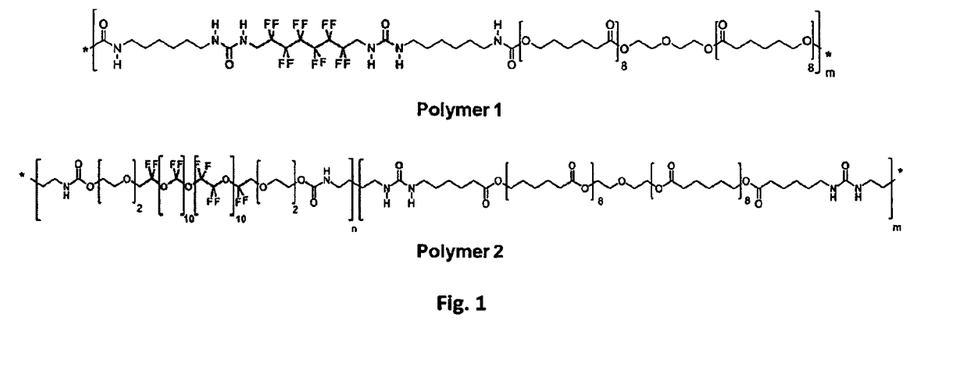
FIG. 1 shows the chemical structure of two fluorinated polymers (Polymer 1 & 2) according to the present invention.

FIG. 1 shows the chemical structure of two fluorinated polymers according to the present invention, viz. Polymer 1 and Polymer 2. Polymer 1 is a block-copolymer of non-fluorinated biocompatible polycaprolactone blocks and perfluorinated blocks linked by means of urea spacers forming physical crosslinking groups. Polymer 2 is a block-copolymer of non-fluorinated biocompatible polycaprolactone blocks and fluorinated polyether blocks linked by means of urea spacers forming physical crosslinking groups.

Figure 2:
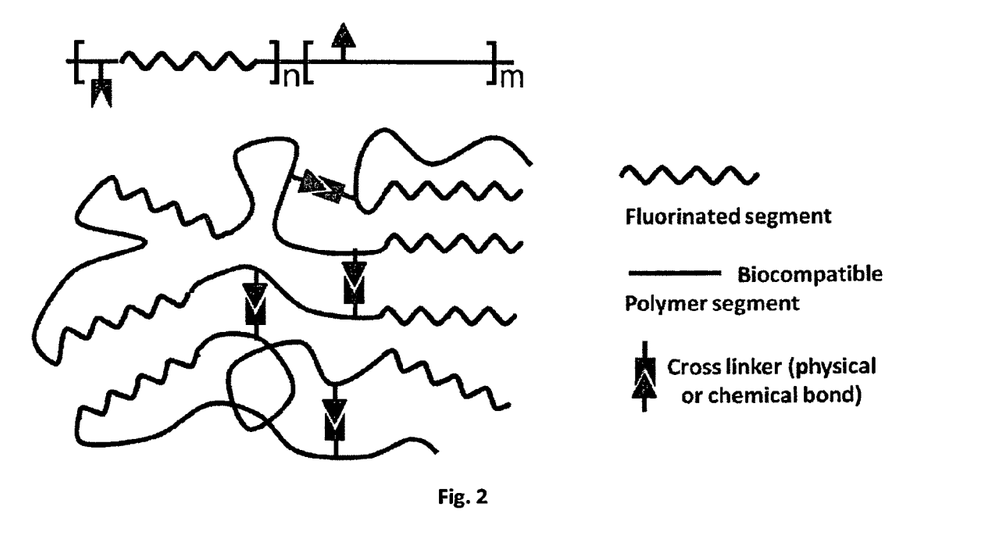
FIG. 2 is a schematic representation of a polymeric network of one embodiment of the present invention.

FIG. 2 is a schematic representation of a polymeric network formed by several molecules of Polymer 1 or Polymer 2. The wavy part depicts the fluorinated segment (i.e. the (per)fluorinated blocks). The solid line depicts the non fluorinated segment (i.e. the polycaprolactone blocks). The non-fluorinated and fluorinated segments are covalently linked as is clear from FIG. 1. The combination of the triangle and crown-shaped receiving element depict the crosslinking groups (i.e. hydrogen bonds), which cross linking is optional in the case of covalently linked fluorinated copolymers, such as Polymer 1 and Polymer 2.

Figure 3:
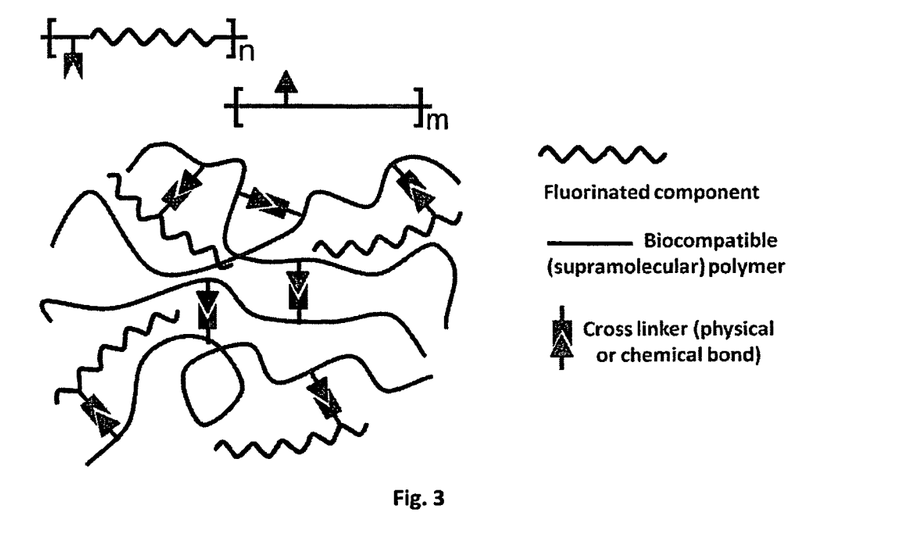
FIG. 3 is a schematic representation of a polymeric network of another embodiment of the present invention.

FIG. 3 shows an alternative strategy for building a fluorinated polymer network. In this strategy there is no covalent bond between the fluorinated and non fluorinated segments. The wavy part depicts the fluorinated segment (i.e. the (per)fluorinated blocks). The solid line depicts the non fluorinated segment (i.e. the polycaprolactone blocks). The combination of the triangle and crown-shaped receiving element depict the crosslinking groups (i.e. hydrogen bonds). This strategy is hence based on bisurea functionalized polycaprolactone that is able to bind to (small) fluorinated moieties, due to hydrogen bonding interactions. Polymeric fibers are thus functionalized with $^{19}$F labels.

The presented fluorinated copolymers and supramolecular polymers are mostly insoluble in water and they display mechanical properties that provide adequate structural support for in vitro or in vivo cell growth. In a solid object formed of these copolymers, the fluorinated polymers form the imaging component and the non-fluorinated polymers form the structural component. The mechanical properties of these fluorinated polymers can be tuned by the presence of so-called "crosslinking" groups that allow for intermolecular interactions via covalent bonds or through the establishment of hydrogen bonding units, such as amide, urethane, or urea-units, for example. These crosslinking groups can also be used for further incorporation of biologically active groups to promote cell adhesion and cell differentiation on the tissue engineering scaffold.

Figure 8:
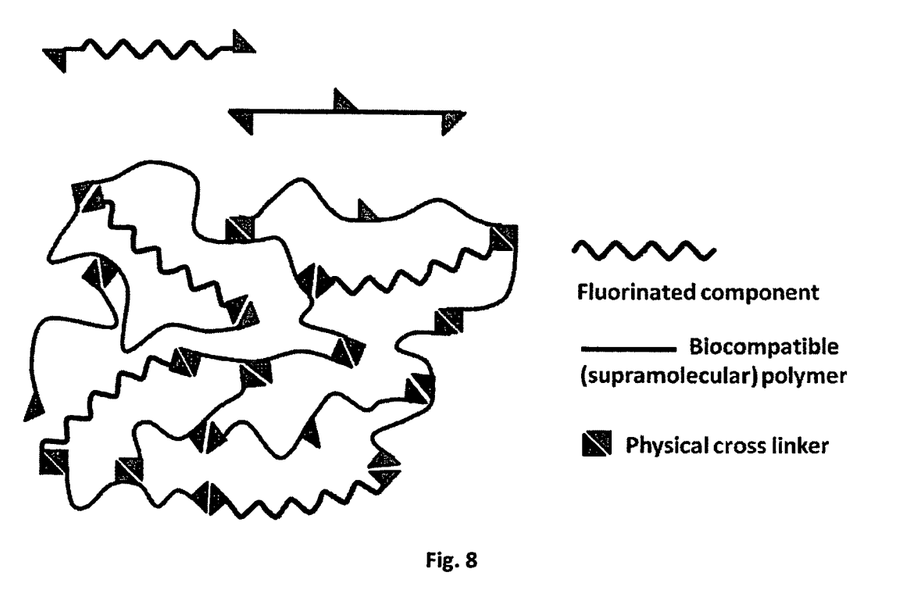
FIG. 8 is a schematic representation of a supramolecular polymeric network of yet another embodiment of the present invention.

FIG. 8 shows a non-limiting example of an alternative strategy for building a fluorinated supramolecular polymer network, comprising a plurality of non-fluorinated oligomers (solid lines) each comprising at least three crosslinking units (half squares) and a plurality of fluorinated oligomers (wavy lines) each comprising at least two crosslinking units (half squares). A supramolecular polymeric network is obtained by strong interactions between the complementary crosslinking units (half squares) such as for example ureidopyrimidone or bis-urea units.

In the embodiment of the present invention in which supramolecular polymers are used, the fluorinated polymer comprises highly fluorinated polymeric units (A), such as fluorinated polyester, fluorinated poly(meth)acrylate, fluorinated silicones or fluorinated polyether, for example comprising typically at least 5 wt % fluorine atoms per polymeric unit, which units (A) are functionalized by at least two chemical groups (i.e. crosslinking units) allowing self-assembly or recognition (x). Preferred groups (x) are α,ω-bis(ureido)alkyl groups, α,ω-bis(ureido)aryl groups, or ureidopyrimidone-derivatives, such as 2-ureido-6-alkyl isocytosine and 2-ureido-5-(2-hydroxyethyl)-6-alkyl isocytosine. Preferably, (x) is a ureidopyrimidone derivative. The general structure of the supramolecular polymer can for example be: . . . x-A-x . . . x-A-x . . . x-A-x . . . x-A-x . . . , wherein . . . stands for a physical crosslinking group. Said fluorinated supramolecular polymer has a Young's modulus that is at least 0.1 mega Pascal (MPa), preferably at least 1 MPa, most preferably at least 5 MPa. In this embodiment of the invention, the polymeric units (A) preferably have a molecular mass in between 600 and 10,000 gram/mol, more preferably in between 1500 and 6000 gram/mol, even more preferably in between 2000 and 4500 gram/mol.

In yet another embodiment, the fluorinated supramolecular copolymer comprises a first fluorinated supramolecular polymer comprising units of at least one fluorinated polymer or oligomer (A) and at least two chemical groups (x) that allow self-assembly or recognition and a second non-fluorinated supramolecular polymer comprising units of at least one non-fluorinated polymer or oligomer (Y) and at least two chemical groups (x) that allow self-assembly or recognition. Preferably, the second non-fluorinated polymer comprises at least three chemical groups (x), more preferably four. In a preferred embodiment of this invention, the polymeric (Y) has a molecular mass in between 1250 and 40,000 gram/mol, more preferably in between 2000 and 20,000 gram/mol, even more preferably in between 3000 and 15,000 gram/mol.

This type of fluorinated polymer is mostly insoluble in water and display mechanical properties that can be readily tuned by mixing these types of fluorinated polymers with similar supramolecular (non-) fluorinated polymers at various ratios (for instance, a supramolecular polymer x-Y-x where Y is non-fluorinated). The general structure of such a supramolecular copolymer can for example be: . . . x-A-x . . . x-Y-x . . . x-A-x . . . x-Y-x . . . .

Figure 9:
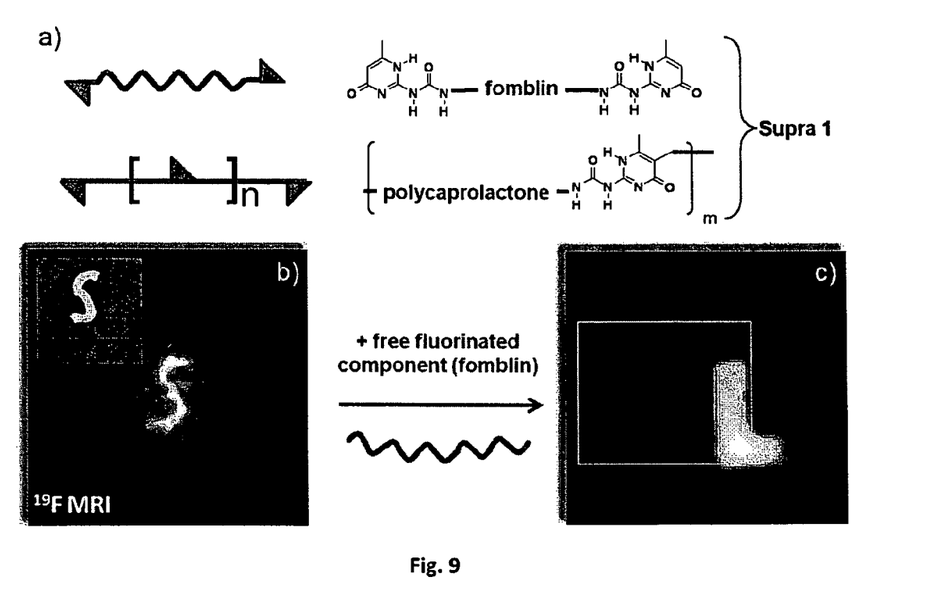
FIG. 9(a) shows an example of the chemical structure a supramolecular polymer (Supra 1) according to the invention.
FIG. 9(b) is a $^{19}$F MRI image of Supra 1.
FIG. 9(c) is a $^{19}$F MRI image of the co-extrusion product of Supra 1 and a perfluorinated polyether (e.g. an oil from the Fomblin®-series).

Supramolecular polymers based on fluorinated blocks modified with chemical functions capable of self-assembly (FIGS. 8 and 9) were also developed and tested. The general structure of such materials is depicted in FIG. 9. The fluorinated molecules can be mixed with non-fluorinated molecules to adjust mechanical and cell adhesion properties. Both the fluorinated and non-fluorinated materials are functionalized with quadruple hydrogen bonding ureidopyrimidinone (so-called UPy) moieties, where these moieties self assemble and therefore give rise to an increase in the virtual molecular mass of the supramolecular polymers. Materials exhibiting a diverse range of mechanical and biological properties can be obtained, using a modular approach, by simply mixing different ratios of these UPy-functionalized materials. FIG. 9c illustrates that the supramolecular polymers, by way of the presence of the fluorinated blocks, can be plasticized with fluorinated oils such as for example with (per)fluoroalkanes or (per)fluoro-polyethers. This plasticizing strategy results in a further contrast increase, and can also be applied to the previously presented fluorinated copolymers (e.g. those presented in FIGS. 2 and 3, particularly materials of the type of Polymer 2).

Figure 10:
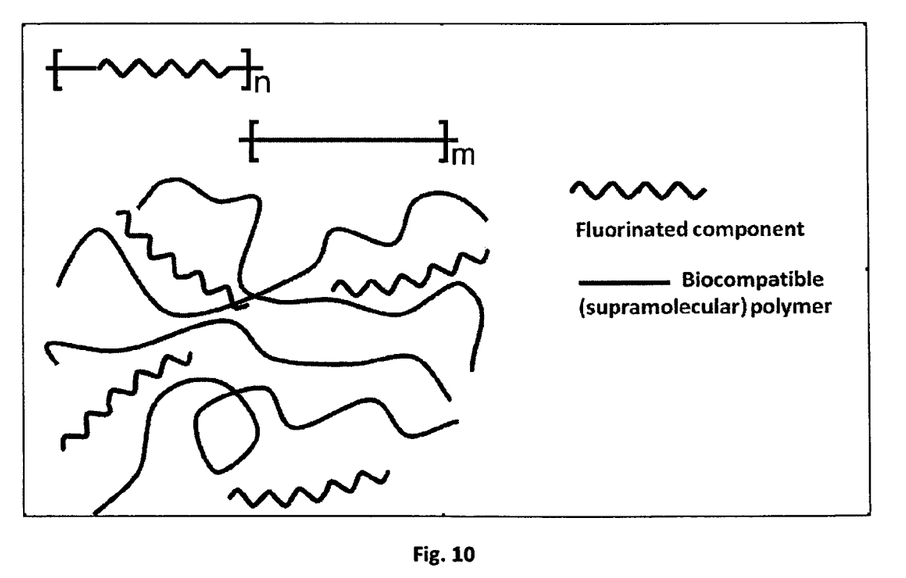
FIG. 10 is a schematic representation of a network of yet another embodiment of the present invention, viz. a mixture of polymers (e.g. Mix 1)

In yet another embodiment of this invention, the solid object comprises a blend of a fluorinated polymer with a non-fluorinated polymer, in which the fluorinated polymer has a glass transition temperature below 40° C., preferably below body temperature, or even below 20° C., or even below 0° C., most preferably below −40° C. This is schematically depicted in FIG. 10 which shows a fluorinated polymer network, comprising a plurality of non-fluorinated polymers (solid lines) and a plurality of fluorinated polymers (wavy lines), which polymers are mixed together. The non-fluorinated parts can for example be based on high molecular mass aliphatic polyesters, polycarbonates, and poly(orthoesters), such as poly(caprolactone), poly(L-lactic acid), poly(D,L lactic acid), poly(glycolic-co-lactic acid) and copolyesters thereof, and poly(trimethylenecarbonate). Otherwise, the non-fluorinated polymers may be (co)-polyesters, (co)-polycarbonates, supramolecular polyesters or supramolecular polycarbonates comprising ureidopyrimidone, urea and/or bisurea units, where the supramolecular polymers preferably have a lower molecular mass. In this embodiment, the fluorinated polymers have preferably a mass from about 600 to about 15,000 gram/mol, more preferably from about 1000 to about 4500 gram/mol. Preferably, the fluorinated polymer is selected from the group consisting of perfluoroalkanes, perfluoroarenes, and perfluoropolyethers (PFPE). PFPE's are known in the art and preferably comprise monomeric units selected from —$OCF_2$—, —$OCF_2CF_2$—, —$OCF_2CF(CF_3)$—, —$OCF_2CF_2CF_2$—, and/or —$OCF_2CF_2CF_2CF_2$—. Commercially available examples of such PFPE's are Galden® D02 TS, Fomblin® HC-series, Fomblin® HV 25/9, Fomblin® Y-series, Fomblin® W-series, Fomblin® Z-series, Krytox® 143-series, and Demnum® S-series. Most preferably, the fluorinated polymer is a perfluoropolyether. Accordingly, in this specific embodiment, the fluorinated polymer may have high fluor contents that may exceed 50 wt % or even 60 wt %.

The molecular mass of the non-fluorinated component in the blend is in between 2000 and 200,000 gram/mol, preferably in between 40,000 and 150,000 gram/mol, more preferably in between 60,000 and 100,000 gram/mol.

These mixtures of fluorinated and non-fluorinated polymers are mostly insoluble in water and they display mechanical properties that provide adequate structural support for in vitro or in vivo cell growth. In a solid object formed of such a polymers mixture, the fluorinated polymers form the imaging component and the non-fluorinated polymers form the structural component.

The present invention moreover relates to a solid object comprising a structural component and an imaging component, in which the imaging component is at least one fluorinated polymer having a glass transition temperature (Tg), preferably determined by differential scanning calorimetry, of below 40° C., preferably below 20° C., more preferably below 0° C., even more preferably below −40° C. The solid object is, for example, a scaffold suitable for tissue engineering. The imaging component is comprised of at least one fluorinated polymer according to the present invention as disclosed above. All embodiments already described above also apply to the solid object.

The fluorinated compound, oligomer or polymer may act both as an imaging component and as a structural component, i.e. the imaging component may provide some or all of the structural properties that are desired. More preferably, however, at least one non-fluorinated polymer is present in the solid object as the structural component besides the at least one fluorinated polymer as the imaging component.

In yet another embodiment, the present invention relates to a scaffold in which the structural component is selected from the group, consisting of a polymer, a covalently or non-covalently bonded copolymer, and one or more mixtures or combinations thereof.

In yet another embodiment, the structural component of the solid object or the total solid object is obtained by means of solvent casting, dip-coating, freeze-drying, precipitation casting, spray coating, painting, roll-coating, foaming, solvent spinning, wet spinning, (cryo)electro-spinning, microcontact printing, ink jet printing, particulate-leaching techniques, phase-separation techniques or emulsion processes. Preferably, the structural component of the solid object or the total solid object is obtained by means of electrospinning. Electrospinning uses an electrical charge to draw very fine fibres from a liquid in which the polymer or polymers have been dissolved. The fibres can for example be on micrometer or nanometer scale.

In yet another embodiment, the structural component of the solid object or the total solid object is obtained by means of extrusion, reactive-extrusion, micro-extrusion, fused deposition modelling, molding, lamination, film-blowing, reaction injection molding (RIM), spinning techniques, rapid prototyping. or by thermal or photocuring of a coating.

In yet another embodiment, the present invention relates to a solid object or scaffold in which the Young's modulus of the structural component is at least 0.1 mega Pascal (MPa), preferably at least 1 MPa, most preferably at least 5 MPa. This allows for the manufacturing of solid objects or scaffolds that are of adequate strength that is required for the solid object or scaffold to perform their desired functions. The Young's modulus or tensile modulus is a measure of the stiffness of an isotropic elastic material.

In yet another embodiment, the present invention relates to a fluorinate polymer that has a Young's modulus that is at least 0.1 Mega Pascal (MPa), preferably at least 1 MPa, more preferably at least 5 MPa. This allows for the manufacturing of solid objects or scaffolds that are of adequate strength to perform their desired function. The Young's modulus or tensile modulus is a measure of the stiffness of an isotropic elastic material.

In yet another embodiment, the present invention relates to a solid object or scaffold in which:
  the structural component is present in an amount of 0 to 99 wt %, preferably 75 to 95 wt %, more preferably 80 wt % to 92 wt % based on the total mass of the scaffold,
  the imaging component is present in an amount of 1 to 100 wt %, preferably 2 to 25 wt %, more preferably 4 to 20 wt % based on the total mass of the scaffold,
  a biologically active component is optionally present in an amount of 0 to 50 wt %, preferably 0.1 to 10 wt % based on the total mass of the scaffold.

The present invention moreover relates to the use of a scaffold as described above as a substrate for growing an element selected from the group of a tissue, a heart valve, a heart patch, one or more blood vessels or a connection thereof or as a nerve guide, prosthesis, or implant.

In addition, the present invention relates to a method for $^{19}$F magnetic resonance imaging (MRI) in solid state using a contrast agent comprising a fluorinated polymer having a glass transition temperature (Tg) below 40° C., preferably below 20° C., more preferably below 0° C., even more preferably below −40° C. The Tg is preferably measured by DSC. All embodiments disclosed above for the use are also applicable as regards this method.

In addition, the present invention relates to a method for in vivo visualization of a solid object or scaffold according to the present invention, said method comprising the steps of:
  providing a solid object or scaffold according to the present invention;
  surgically inserting said solid object or scaffold into a human or animal body;
  visualizing said solid object or scaffold using $^{19}$F magnetic resonance imaging (MRI).

All embodiments disclosed above for the use are also applicable as regards this method. This method thus relates to real time in vivo visualization of a solid object or scaffold according to the present invention.

This can be used, for example, when a solid object is inserted into a body and the precise location after implantation is to be confirmed in order to make sure the solid object is present at the intended location.

In addition, the present invention relates to a method for in vivo monitoring the degradation of a solid object or scaffold in time, in which the solid object or scaffold according the present invention is used and in which the degradation is monitored in time by using $^{19}$F magnetic resonance imaging (MRI) and $^{19}$F magnetic resonance spectroscopy (MRS) to visualize the solid object or scaffold and in which the amount of degradation of the solid object or scaffold is determined based on the decrease in the visibility of the amount of $^{19}$F.

This can be used, for example, when a solid object or scaffold is inserted into a body and it is desirable that this solid object or scaffold degrades in time and their place is taken over by newly grown body cells. In that case, not only the precise location after implantation can be confirmed, but also the degradation can be fully monitored until there is no longer any fluorinated polymer visible, i.e. when the degradation has progressed to such an extent that it is below the visibility limit, i.e. until the solid object has nearly or completely degraded.

When the fluorinated polymers, the solid objects or scaffolds according to the present invention degrade in vivo, the breakdown products are non-toxic and are metabolized or removed by the body by process known to a person skilled in the art.

The product and use according to the present invention as disclosed in the appended claims relate to the field of in vivo imaging of tissue engineering constructs. The inventors propose the use of fluorinated polymers, copolymers or supramolecular polymers as imaging labels suitable for tissue engineering scaffolds. As mentioned above, the strategy of the present inventors focuses on the development of materials containing fluorine units having a high mobility while the fluorine units are in the solid state. This is achieved by the fluorinated polymers having a glass transition temperature (Tg) below 40° C., preferably below 20° C., more preferably below 0° C., even more preferably below −40° C. The Tg is preferably determined by differential scanning calorimetry. This maximum value for the glass transition temperature allows materials having low-temperature phase transitions for the fluorine units and with fluorine units having adequate flexibility and mobility, e.g. because of the existence of non-covalent bonds in the case of supramolecular polymers. This allows measurement of these fluorinated polymers at body temperature.

Advantages of the present invention are that they allow a quantitative method, that there is no fluorine background signal to be found in the body, and thus no artefacts coming from other tissues. Another advantage is that imaging in the solid state is possible and that there is no need for injection of a contrast agent, since the latter is intrinsically part of the scaffold. Moreover, there is a good processibility of the materials. Compared to CT or Ultrasound imaging, MRI has a very good resolution and is in particular suitable for tissue visualization. This solution, using $^{19}$F MRI, offers the advantage of the use of contrast agents, which we believe are less toxic in the long run compared to commonly used agents for $^{1}$H MRI.

As mentioned above, the present invention is applicable in the field of tissue engineering for monitoring follow post-implantation remodelling of tissue engineering constructs and in-vivo degradation of scaffold materials in relation to the growth and remodelling of newly formed tissue. The polymers and polymer blends described in the present specification can be easily processed in a fibrillar meshwork allowing the fabrication of scaffolds for applications such as artificial heart valves or vascular grafts, but are not limited thereto (they could also be all kinds of scaffolds used for other organs/devices/objects). The monitoring can be performed with clinical MRI scanners equipped with the necessary coils and software for $^{19}$F MRI.

The present invention will be elucidated below using the following examples, which are merely for illustrative purposes and which are not intended to limit the scope of the claims.

Examples

In examples of the present invention, polymers containing alternating units of either a fluorinated alkylene, e.g. $(CF_2)_6$, (Polymer 1) or a fluorinated polyether, e.g. of the class of commercially available perfluoropolyethers marketed under the trade name of Fomblin® (Polymer 2) on the one hand, and polycaprolactone based segments on the other hand, have been prepared. To ensure good mechanical properties, urea units were embedded in the polymer chain, which urea units may lead to crosslinking intermolecular hydrogen bonds (i.e. physical crosslinking).

The content of fluorine in the investigated fluorinated polymers was about 9 wt % for both Polymer 1 and Polymer 2, as based on the total mass of the respective copolymers. The fluorine content can be calculated by taking into account the amount of reactants that have been used to prepare the materials, and these calculated fluorine contents have been given in these examples. Alternatively, the fluorinated contents can experimentally be determined in a $^{19}F$ NMR assay using an internal standard that contains fluorine atoms (e.g. HFIP). The inventors have found that these types of assays provide comparable, if not somewhat higher, values as those that have been calculated.

FIG. 1 illustrates the general structure of Polymer 1 and Polymer 2. FIG. 2 shows a schematic representation of the polymer network of a fluorinated polymer such as Polymer 1 or Polymer 2. Both co-polymers consist of alternating units of fluorinated blocks and (bio)-polymer segments, which are rigidified by physical crosslinking groups.]

Synthesis of Polymer 1

The fluorinated diamine 1,8-diamino-2,2,3,3,4,4,5,5,6,6,7,7-dodecafluorooctane required for the synthesis of Polymer 1 was synthesized according to a modified procedure as previously described by Greenwald (J. Org. Chem., 41, 1469 (1976)). Briefly, the commercially available 1,8-dihydroxy-2,2,3,3,4,4,5,5,6,6,7,7-dodecafluorooctane was tosylated with an excess of tosyl chloride (1.5 equivalents) in pyridine at 4° C. The tosylate was isolated by aqueous work-up (extraction with ether), followed by crystallization in ethyl acetate, and was subsequently reacted for 24 hrs. with $NaN_3$ in DMSO at 120° C. The reaction mixture was poured in water, and the diazide product (an oil) was isolated by extraction with ethyl acetate and evaporation of the solvent. Finally, the diazide was hydrogenated in ethanol using hydrogen pressure (50 Psi) and a Pd/C catalyst, giving the diamine solid product.

Poly-caprolactone diol (PCL, $M_n$=2000, 20 g, 10 mmol, initiated by ethylene glycol) was dried under vacuum at 80° C. for 5 hours. Subsequently, 1,6-diisocyanatohexane (10 g, 59.5 mmol) was added to the molten polymer and the resulting mixture was stirred at 80° C. under an argon atmosphere for 16 hours. The resulting reaction mixture was poured in 500 mL n-hexane. The resulting precipitate was collected by filtration and dried in vacuo to yield 19.0 g (81%) of the desired PCL diisocyanate building block.

The peaks in the $^1H$-NMR spectrum using deuterated chloroform as reference are as follows: ☐=4.69 (broad singlet for NH), 4.21 (triplet for $OCH_2$ of the diethylene glycol initiator), 4.04 (triplet for $OCH_2$ of caprolactone), 3.68 (triplet for $OCH_2$ of the ethylene glycol initiator), 3.28 (triplet for $CH_2NCO$), 3.14 (broad multiplet for $CH_2NH$), 2.29 (triplet for $CH_2CO$ for caprolactone), 1.8-1.2 (broad multiplet) ppm.

The peaks found using Infrared Spectroscopy in the Attenuated Total Reflection Mode (i.e. IR(ATR)) are as follows: ☐=3386 (NH), 2939, 2864 (CH), 2270 (NCO), 1728 (C=O), 1235, 1161 $cm^{-1}$.

The PCL diisocyanate obtained above (4.6 g, 2 mmol) was dissolved in 20 mL dry THF and was stirred under an argon atmosphere. The fluorinated diamine 1,8-diamino-2,2,3,3,4,4,5,5,6,6,7,7-dodecafluorooctane (0.70 g, 2 mmol), synthesized according to a modified procedure as previously described by Greenwald (J. Org. Chem., 41, 1469 (1976)) was added slowly in 10 mL dry THF. The reaction mixture was allowed to stir for 4 hours at room temperature and a further 16 hours at reflux. The solvent was subsequently removed using rotary evaporation and the resulting solid was stirred with 100 mL methanol, decanted and dried. The resulting solid was dissolved in a mixture of chloroform and methanol (2:1) and precipitated in cold ether, affording 2.93 g (55%) of Polymer 1.

The peaks in the proton NMR spectrum using DMSO-$d_6$ as reference are as follows: ☐=6.99 (broad singlet for NH), 6.33 (broad singlet for NH), 6.12 (broad singlet for NH), 4.09 (multiplet for $OCH_2$ of the ethylene glycol initiator), 3.96 (triplet for $OCH_2$ of caprolactone), 3.87 (multiplet for $CH_2NH$), 3.58 (multiplet for $OCH_2$ of the ethylene glycol initiator), 3.1-2.8 (broad multiplet for $CH_2NH$), 2.25 (triplet for $CH_2CO$ of caprolactone), 1.7-1.1 (broad multiplet) ppm.

The peaks in the $^{19}F$ NMR spectrum using DMSO-$d_6$ as solvent are as follows: ☐-113, -117, -119 ppm. The fluorine content in Polymer 1 is approximately 9 wt %.

The peaks found using Infrared Spectroscopy in the Attenuated Total Reflection Mode (i.e. IR(ATR)) are as follows: ☐3357 (NH), 2937 (CH), 2864 (CH), 1726 (C=O), 1650-(C=O), 1574, 1537, 1237, 1161 $cm^{-1}$.

Using Gel Permeation Chromatography (GPC) in HFIP the number average molecular mass (Mn) was determined to be 32 kg per mol as compared to polymethyl methacrylate (PMMA) reference standards. The polydispersity index (PDI) was found to be 2.8.

The glass transition temperature of the Polymer 1 material was found to be approximately -50° C., as determined by DSC. With DSC broad melting transitions around 45° C. and 80° C. have also been recorded.

Measurements on Polymer 1

Figure 4:
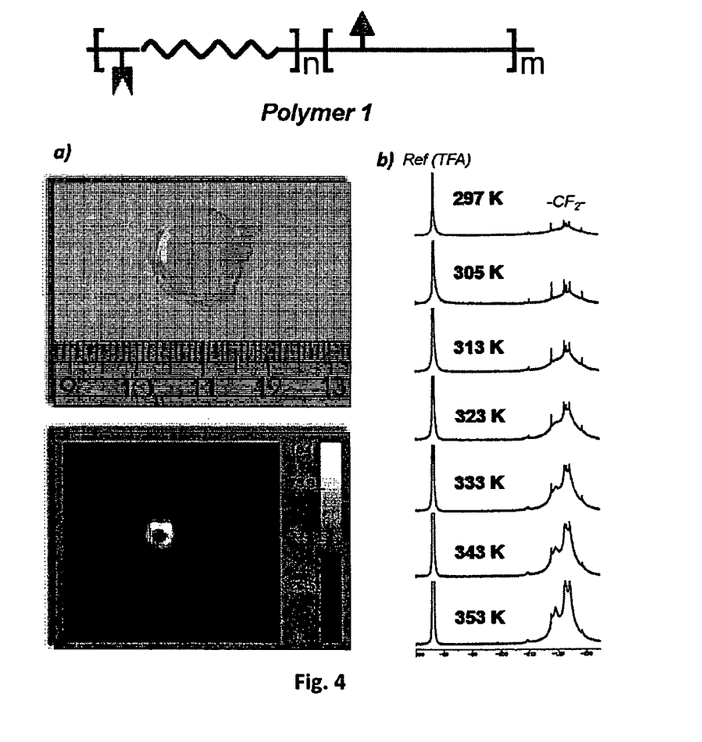
FIG. 4(b) shows a temperature-dependent $^{19}$F NMR study of Polymer 1 in solid state.

Polymer 1 according to the present invention was easily solubilised in organic solvents such as chloroform, tetrahydrofuran or hexafluoro isopropanol. After evaporation of the solvent, a solid disc of approximately 600 milligram was obtained, which disc was immersed in water. The disc was analyzed with $^{19}F$ NMR in the solid state. As shown in FIG. 4(b), the $^{19}F$ NMR experiment Polymer 1 revealed an increasing and sharper fluorine signal with increasing temperature around -115 ppm; the reference is TFA. The fluorinated polymer has been immersed in the solid state in a $D_2O$ solution containing 0.05% (trifluoro acetic acid) TFA (having a singlet peak at -76 ppm). This increase and sharpening of the signal is due to increasing mobility of the fluorine units in the polymer matrix with increasing temperature. Notably, Polymer 1 still remained in the solid state. The intensity of the signal was also directly proportional to the amount of material, which shows that such polymer is appropriate for quantitative studies.

FIG. 4(a) shows a photo of a solid object of Polymer 1 prior to insertion in an MRI apparatus (top view) and a $^{19}F$ MRI image thereof at 37° C. (bottom view).

Even though the fluorine blocks were not entirely melted at body temperature (complete phase transitions at approximately 45° C. and approximately 80° C.), this fluorinated polymer was successfully imaged in clinical conditions at a temperature of 37° C. in the solid state; there was no need for an external contrast agent. $^{19}F$ MRI indeed confirmed the visibility of the solid disc as shown in FIG. 4(a). This fluorinated polymer could also be electrospun from a 300 mg/nL solution in HFIP (hexyluoro-2-propanol) thus providing a meshwork of polymeric fibres in the micrometer range. Such an open mesh is desirable for cell proliferation.

Synthesis of Copolymer Materials of the Type of Polymer 2

A mixture of 1,4-diisocyanatobutane (220 mg, 1.88 mmol) and ethoxylated poly(tetrafluoroethylene oxide-co-difluoromethylene oxide) α,ω-diol (Mn=2.2 kg mol$^{-1}$, 0.20 g, 0.09 mmol) was heated at 80° C. under an argon atmosphere for 2 hours. The resulting mixture was allowed to cool before being dissolved in 1.5 mL dry tetrahydrofuran to obtain an isocyanate solution, named solution A.

Separately, a carbobenzyloxy-protected polycaprolactone α,ω-diamine (Mn=2.88 kg mol$^{-1}$, 5.42 g, 1.88 mmol) was prepared according to the publication in Biomacromolecules 7, page 3385 (2006).

Subsequently, the product was deprotected by means of hydrogenolysis using 10% palladium on carbon in 70 mL of a 5:2 mixture of ethylacetate and methanol. After completion of the hydrogenolysis reaction, the obtained reaction mixture was filtered over diatomaceous earth (e.g. Celite®) and evaporated to a final volume of approximately 30 mL.

The deprotected polycaprolactone α,ω-diamine was then precipitated with n-hexane, dried after decantation of the solvent, and subsequently redissolved in 15 mL dry chloroform. The resulting isocyanate solution A that was obtained previously was added slowly to this polycaprolactone α,ω-diamine solution in chloroform under constant stirring under an argon atmosphere. The reaction mixture was allowed to stir for another 16 hours under argon, before the solvents were removed by rotary evaporation.

The resulting solid was stirred with 50 mL of methanol, the solvent was decanted and the product was dried to afford 3.7 g (75%) of a material of the type of Polymer 2.

The peaks in the proton NMR spectrum using acetone-d$_6$ as reference are as follows: δ=8.5 (broad singlet for NH), 5.7 (broad singlet for NH), 4.18 (triplet for OCH$_2$, diethylene glycol initiator), 4.05 (triplet for OCH$_2$, caprolactone), 3.68 (triplet for OCH$_2$, diethylene glycol initiator), 3.12 (broad multiplet for CH$_2$NH), 2.31 (triplet for CH$_2$CO), 1.7-1.2 (broad multiplet) ppm. It should be noted that the protons of the 5% perfluoroether in the copolymer are not visible.

The peaks in the fluorine NMR spectrum using acetone-d$_6$ as reference are as follows: δ=−56.8, −47.3, −48.9, −50.0, −50.6, −51.8, −73.2, −75.4, −84.0, −84.3, −85.3, −86.1, −87.0 ppm. The fluorine content of this particular Polymer 2 material is approximately 2 wt %, The peaks found using Infrared Spectroscopy in the Attenuated Total Reflection Mode (i.e. IR(ATR)) are as follows: ν=3336 (NH), 2943 (CH), 2866 (CH), 1721 (C=O), 1624 (C=O), 1571 (urea), 1471, 1239, 1164 cm$^{-1}$.

Using Gel Permeation Chromatography (GPC) in HFIP the number average molecular mass (Mn) was determined to be 17 kg/mol. The polydispersity index (PDI) was found to be 2.0 with PMMA as a reference standard.

A Tg of the isolated material as determined with DSC was approximately −50° C. This is consistent with the Tg of the amorphous polyester phase. The Tg of the fluoro-ether block was too low to be recorded (at least lower than −50° C.).

In a similar way as described above, other materials of the type of Polymer 2 can be prepared that have a higher fluorine content. This changes the ratio n/m to higher values, see FIG. 1. Such can be achieved by using relatively less of the 1,4-diisocyanatobutane building block, while using more of the fluoroether building block. In this fashion, a Polymer 2 material has been prepared with a fluorine content of approximately 9 wt %; this Polymer 2 has been examined in more detail, and results have been reported on hereunder.

Measurements on Polymer 2

Figure 5:
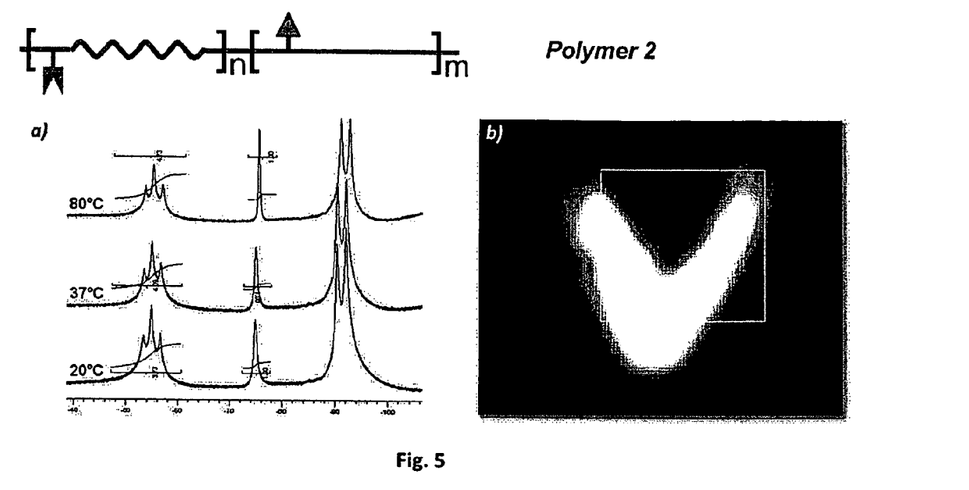
FIG. 5(a) shows a temperature-dependent $^{19}$F NMR study of Polymer 2 in solid state.
FIG. 5(b) is a $^{19}$F MRI image of Polymer 2 shaped in a "V"

FIG. 1 also shows the chemical structure of Polymer 2 according to the invention based on a polycaprolactone polymer containing fluorinated polyether segments. FIG. 5(a) is temperature dependent $^{19}$F NMR study of Polymer 2 containing 9 wt % fluorine. An amount of 150 mg of Polymer 2 was immersed in solid state in a deuterium oxide solution containing 0.05% trifluoro acetic acid (singlet at −76 ppm). Interestingly, the two signals originating from the polymer at −55 ppm and −90 ppm were hardly affected by the temperature suggesting a molten state of the fluorinated part of the fluorinated polymer, already at room temperature. The intensity of these two signals at −55 ppm and −90 ppm was comparable to those measure with Polymer 1 at a high temperature (approximately 80° C.). FIG. 5(b) is a $^{19}$F MRI image of a V-shaped solid object of Polymer 2 at room temperature. The solid object has a mass of 1.6 gram. As shown In FIG. 5(b) the V-shape could be readily imaged in a 3T Philips Scanner, at room temperature, without the need of additional contrast agent. The voxel (i.e. volumetric pixel or Volumetric Picture Element) size is 2 by 2 mm. Therefore, only a few minutes of acquisition is necessary to get the image of FIG. 5(b).

Figure 6:
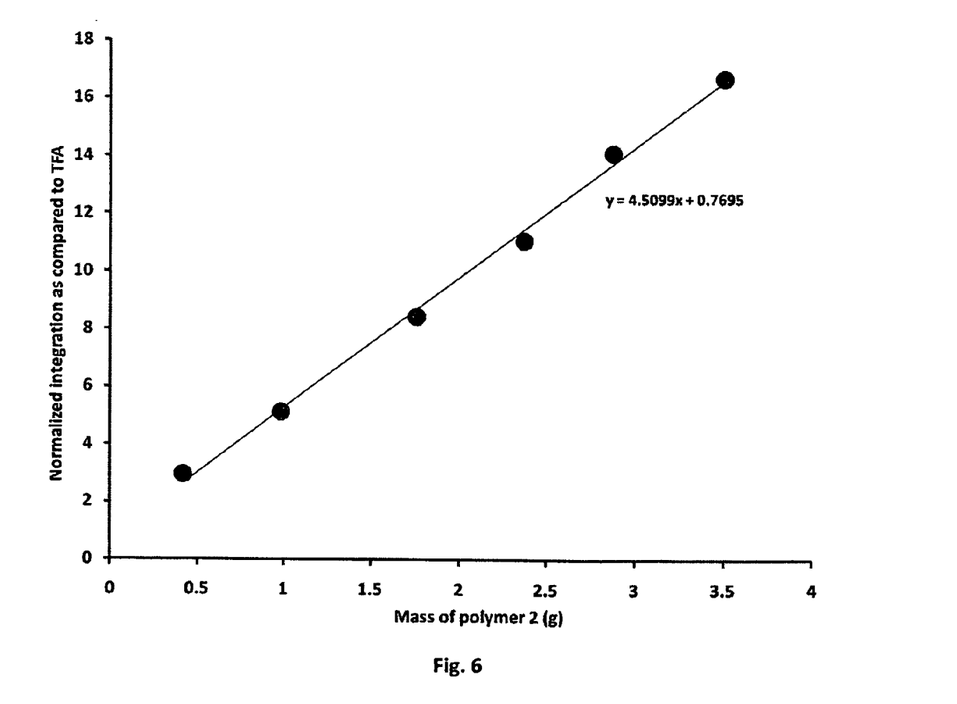
FIG. 6 is a graph depicting the normalized integration (reference=TFA) of the fluorine signal as measured with $^{19}$F NMR with increasing amounts of Polymer 2 in solid state.
Figure 7:
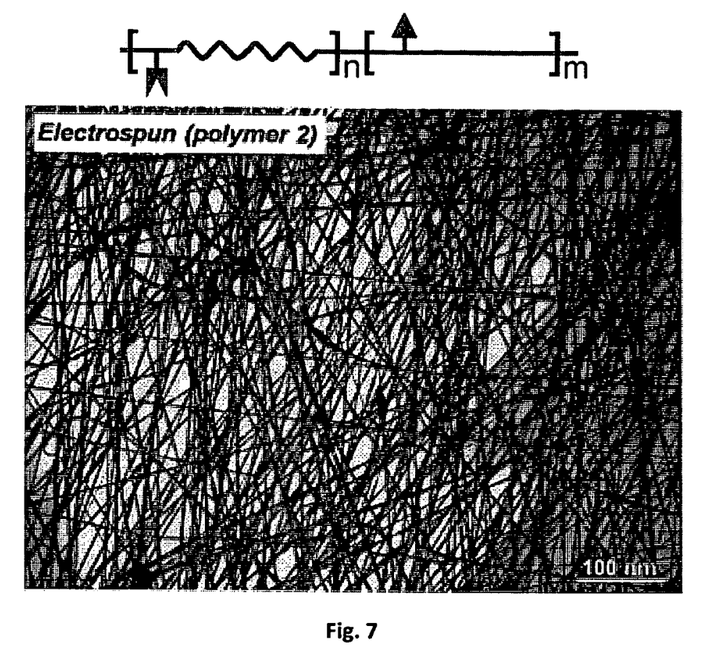
FIG. 7 is an optical microscope photo of electrospun fibres of Polymer 2.

Notably, Polymer 2 could also be successfully electrospun from a HFIP solution at a concentration of 250 mg/mL and with an applied voltage of 18 kV (see FIG. 7). A network of fibres in the micrometer range is obtained. Surface integration of the fluorine signals at −90 ppm with an increasing absolute amount of Polymer 2 (as measured by Magnetic resonance spectroscopy, MRS, against a TFA reference) revealed a linear behaviour in the solid state, therefore making $^{19}$F MRI suitable for quantitative measurements (see FIG. 6).

Preparation of Supra 1

ZDOL 4000 (2.57 g), a methylol terminated poly(tetrafluoroethylene oxide-co-difluoromethylene oxide) α,ω-diol with Mn=4.0 kg mol$^{-1}$ was mixed with isophoronediisocyanate (355 mg) and stirred for 16 h at 80° C. Subsequently, the reaction mixture was heated to 120° C. This was followed by the addition of propylenecarbonate (0.5 mL) and 6-methylisocytosine (200 mg). After stirring for 2 hours under an inert atmosphere, the reaction mixture was cooled to 25° C. upon which a solid separated from the solution. This solid was isolated, dissolved in hot hexafluoroxylene and filtered over Celite®. Subsequent drying in vacuo of the obtained solid resulted in a fluorinated supramolecular polymer as a white rubbery material.

This rubbery fluorinated supramolecular polymer bearing ureidopyrimidone (UPy) groups was blended in a twin-screw extruder at 120° C. with a chain extended polycaprolactone polymer containing UPy-groups, such as those disclosed in patent application EP 1 687 378 (Polymer c4), so that the material Supra 1 was obtained comprising 9.1 wt % of said fluorinated supramolecular polymer and 90.9 wt % of said polycaprolacone polymer modified with UPy-groups.

Measurements on Supra 1

Fluorinated supramolecular polymers based on a central fluorinated polymer block flanked on both sides by ureidopyrimidone (UPy) units (FIG. 9a) have been measured using $^{19}$F NMR and $^{19}$F MRI techniques and showed intense signals with both techniques.

FIG. 8 shows a schematic representation of a polymer network that illustrates the Supra 1 material. The fluorinated polymer unit (wavy line) is physically crosslinked with the non-fluorinated polymer segments (solid line), resulting in the supramolecular polymer material Supra 1.

FIG. 9(b) is a $^{19}$F MRI image of this Supra 1 material at 22° C.

FIG. 9(c) is a $^{19}$F MRI image of Supra 1 co-extruded with a perfluorinated polyether oil (Fomblin® Y06), i.e. the object investigated comprised a blend of the UPy-modified polycaprolactone (89 wt %) with the UPy modified perfluoropolyether (3.8 wt %) and Fomblin® Y06 (7.2 wt %). Both $^{19}$F MRI measurements on Supra 1 containing samples were carried out on samples in the solid state at 22° C.

When the unblended fluorinated supramolecular polymer (containing about 50% $^{19}$F in mass) was placed in a MRI scanner (3T Philips® scanner), this solid was also directly imagable as such.

Preparation of Mix 1

A fluorinated polymer, ethoxylated poly(tetrafluoroethylene oxide-co-difluoromethylene oxide) α,ω-diol (Mn=2. kg mol$^{-1}$) was mixed with polycaprolactone (80,000 gram/mol) in a ratio of 200 mg fluorinated polymer to 1000 mg polycaprolactone and this was dissolved in 4 mL HFIP. The resulting viscous solution was electrospun at a feeding rate of 30 µL/min, under a voltage of 15 kV. The collected sample was dried overnight to ensure full evaporation of the HFIP solvent. The full evaporation of the solvent was confirmed by $^{19}$F NMR. The fluorinated content of Mix 1 was approximately 9 wt %.

Measurements on Mix 1

Figure 11:
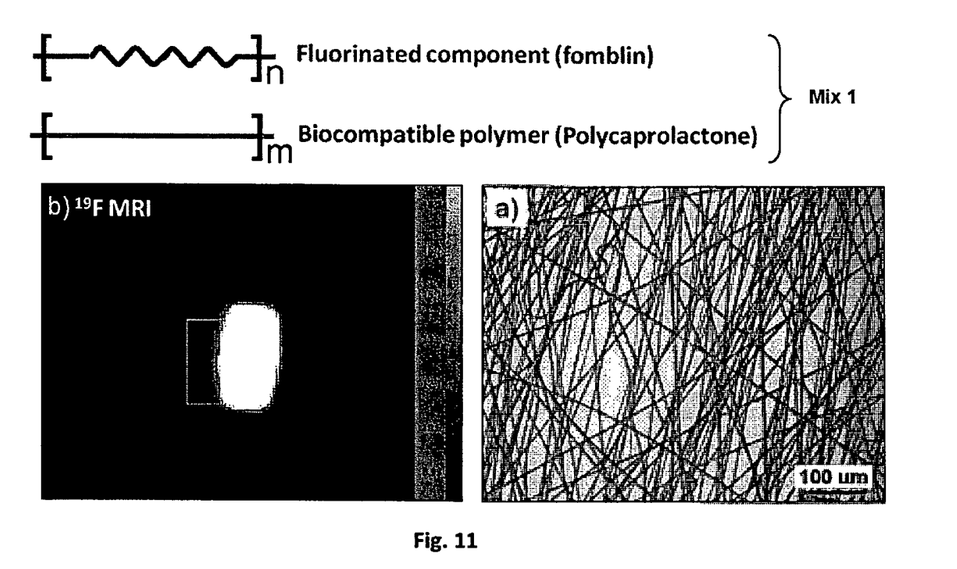

FIG. 10 shows a cartoon example of a blend of a fluorinated polymer (wavy line) mixed with a non-fluorinated polymer (straight line) such as Mix 1. FIG. 11(a) shows a photo of the electrospun fibres forming a porous non-woven or web, which web is usable as a scaffold. FIG. 11(b) is an $^{19}$F MRI image of a solid object of Mix 1. Said solid object was prepared via electrospinning from HFIP in a rectangular shape at room temperature (mass=700 mg).

The above mentioned mixture of fluorinated polymer and PCL was immersed in the solid state in a deuterium oxide solution containing 0.05% trifluoro acetic acid (singlet at −76 ppm). The $^{19}$F NMR signals originating from the polymer at −55 ppm and −90 ppm were very intense, suggesting a high mobility of the fluorinated polymer in the solid object.

Proliferations Tests

The proliferation of the ovine vena saphena cells was investigated on electrospun webs of Polymer 1, Polymer 2, and Mix 1 according to the present invention each comprising approximately 9 wt % of fluorine.

Ovine vena saphena cells were chosen as the intended animal model is the sheep and because these cells are very similar to those involved in the formation of the tissues constituting arteries and heart valves. The cell proliferations were compared to an example not according to the invention, viz. an electrospun web of polycaprolactone (i.e. a material approved by the US Food and Drug Association (FDA)). Polystyrene (PS) was used as a reference standard and was set to 100.

Figure 12:
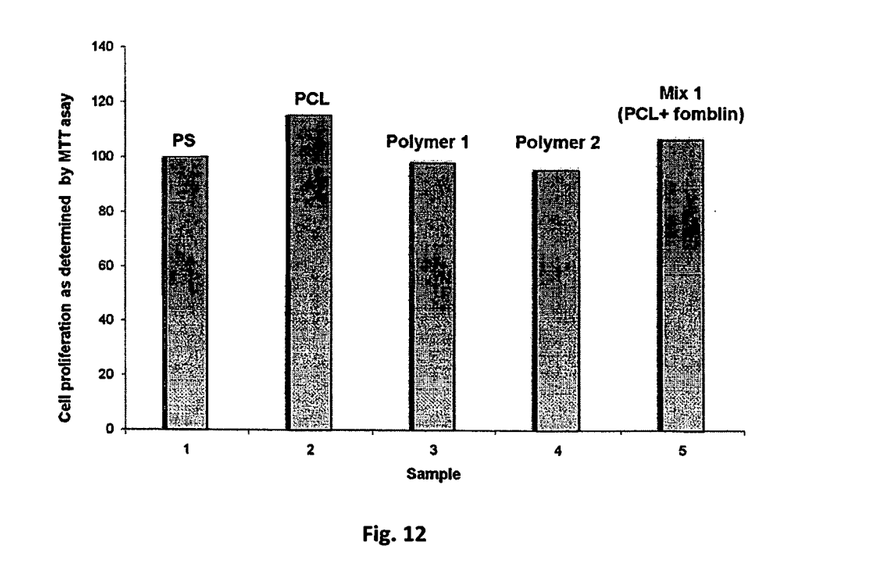
FIG. 12 is a bar diagram showing ovine vena saphena cell adhesion and proliferation assay for several polymers according and not according to the invention.

The results are shown in FIG. 12. From FIG. 12 it is clear that all polymers tested experiments showed similar adhesion rates. Polymer 1 and Polymer 2 according to the invention showed only slightly lower results. These results demonstrate that the incorporation of up to 9 wt % of fluorine does not prevent cells to adhere and proliferate. This result therefore indicates that the fluorinated polymers according to the present invention are not only readily visible by standard imaging techniques at room temperature, but are also suitable for use in tissue engineering procedures.

What is claimed is:

1. A solid object comprising an imaging label or contrast agent including a (per)fluorinated polyether polymer having a glass transition temperature (Tg) below 40° C., which is visible by $^{19}$F magnetic resonance imaging (MRI) of the solid object, wherein the solid object further comprises at least one non-fluorinated polymer wherein the (per)fluorinated polyether polymer and the at least one non-fluorinated polymer are bonded together by covalent or non-covalent bonding, wherein the at least non-fluorinated polymer is obtained from at least one monomer selected from the group consisting of urethane, urea, bisurea, ureidopyrimidone and combinations thereof wherein the amount of fluorine ($^{19}$F) in the (per)fluorinated polyether polymer is at least 5 wt %, based on the total mass of the polymer.

2. The solid object according to claim 1, wherein the (per)fluorinated polyether polymer and the at least one non-fluorinated polymer are bonded together by hydrogen bonding.

3. The solid object according to claim 2, wherein the fluorinated polymer and the at least one non-fluorinated polymer are blended together to form the solid object.

4. The solid object according to claim 1, wherein the (per)fluorinated polyether polymer has a molecular mass of at least 600 gram/mol.

5. The solid object according to claim 1, further comprising a scaffold suitable for tissue engineering including a structural component and the imaging component or contrast agent.

6. The solid object according to claim 5, wherein the structural component is selected from the group consisting of a polymer, a covalently or non-covalently bonded copolymer and one or more combinations thereof.

7. The solid object according to claim 5, wherein the structural component has a Young's modulus of at least 0.1 mega Pascal (MPa).

8. The solid object according to claim 5, wherein: the structural component is present in an amount of 0 to 99 wt %, based on the total mass of the scaffold the imaging component is present in an amount of 1 to 100 wt %, based on the total mass of the scaffold, and optionally a biological active component is present in an amount of 0 to 50 wt %, based on the total mass of the scaffold.

9. The solid object according to claim 1 wherein the at least non-fluorinated polymer is obtained from at least one monomer selected from the group consisting of bis(ureido)alkyl and bis(ureido)aryl.

10. The solid object according to claim 1 wherein the at least non-fluorinated polymer is obtained from at least one monomer selected from the group consisting of bis(ureido)alkyl, bis(ureido)aryl, and ureidopyrimidone.

* * * * *